United States Patent
Epstein

(10) Patent No.: US 6,873,516 B1
(45) Date of Patent: Mar. 29, 2005

(54) SYSTEM FOR PROTECTING A PERSON FROM THE EFFECTS OF ESD

(76) Inventor: Barry M. Epstein, 3 Milford Pl., Dallas, TX (US) 75230

( * ) Notice: Subject to any disclaimer, the term of this patent is extended or adjusted under 35 U.S.C. 154(b) by 213 days.

(21) Appl. No.: 09/934,047

(22) Filed: Aug. 22, 2001

Related U.S. Application Data

(60) Provisional application No. 60/290,695, filed on May 14, 2001.

(51) Int. Cl.[7] .............................................. H05F 3/00
(52) U.S. Cl. ...................................... 361/220; 361/212
(58) Field of Search .............................. 361/212, 213, 361/214, 215, 216, 217, 218, 219, 220–227, 56

(56) References Cited

U.S. PATENT DOCUMENTS

| | | | | |
|---|---|---|---|---|
| 3,587,098 A | * | 6/1971 | Gosnell | 343/915 |
| 3,924,914 A | * | 12/1975 | Banner | 439/105 |
| 4,290,438 A | * | 9/1981 | Price | 132/219 |
| 4,313,148 A | * | 1/1982 | Turner | 361/212 |
| 4,586,106 A | * | 4/1986 | Frazier | 361/212 |
| 4,642,727 A | * | 2/1987 | Dalal | 361/212 |
| 4,654,746 A | * | 3/1987 | Lewis et al. | 361/212 |
| 4,717,349 A | * | 1/1988 | Johnson | 439/92 |
| 4,742,427 A | * | 5/1988 | Richman | 361/230 |
| 4,766,903 A | * | 8/1988 | Esper | 600/300 |
| 4,926,285 A | * | 5/1990 | Reinhardt et al. | 361/230 |
| 4,958,255 A | * | 9/1990 | Pritchard | 361/212 |
| 5,335,137 A | * | 8/1994 | English et al. | 361/220 |
| 5,511,840 A | * | 4/1996 | Allison et al. | 294/64.1 |
| 5,610,526 A | * | 3/1997 | Aslan et al. | 324/522 |
| 5,691,875 A | * | 11/1997 | Dangelmayer et al. | 361/222 |
| 5,768,086 A | * | 6/1998 | Abe | 361/212 |
| 5,844,506 A | * | 12/1998 | Binstead | 341/34 |
| 5,901,022 A | * | 5/1999 | Ker | 361/56 |
| 6,014,037 A | * | 1/2000 | Gabara et al. | 326/30 |
| 6,426,859 B1 | * | 7/2002 | Cohen | 361/220 |

* cited by examiner

*Primary Examiner*—Stephen W. Jackson
*Assistant Examiner*—Danny Nguyen
(74) *Attorney, Agent, or Firm*—Terry M. Gernstein

(57) ABSTRACT

Uncomfortable, disturbing or harmful electrostatic discharge is prevented or reduced by a system which reduces static charges on a person on a periodic basis as the charge is built up. Points of contact are provided which correspond to points the user will contact either by touch or by time-extended contact or continuously in the normal course of operation. The system can be used in mouse pads, the mouse itself, a keyboard, or headphones or earpieces or the like.

45 Claims, 15 Drawing Sheets

FIG. 3K₁.

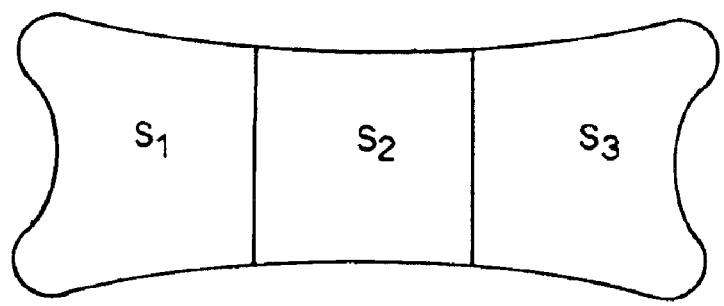
FIG.4A.
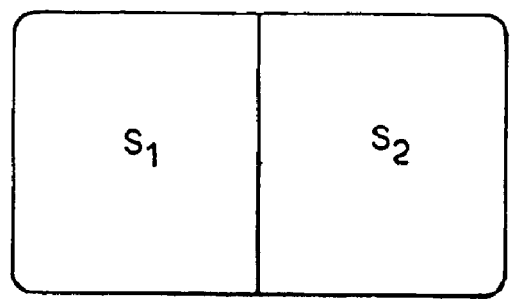
FIG.4B.
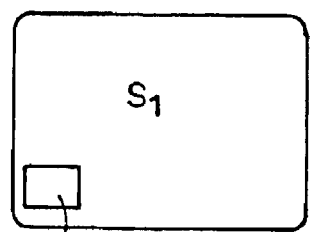
FIG.4C₂
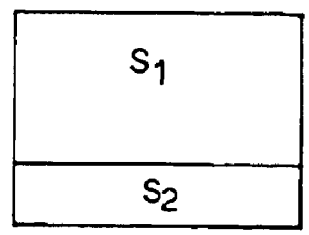
FIG.4C₁

SYSTEM FOR PROTECTING A PERSON FROM THE EFFECTS OF ESD

This Application claims the benefit of Provisional Application No. 60/290,695 filed May 14, 2001.

TECHNICAL FIELD OF THE INVENTION

The present invention relates to the general art of electrical systems and devices, and to the particular field of discharging or preventing accumulation of electric charges.

BACKGROUND OF THE INVENTION

The problem of electrostatic discharge (ESD) is well known. From merely receiving a mild shock after crossing a room and touching a metal object, to sending a shock into electronic equipment, nearly everyone has experienced an ESD problem at some time.

While static electricity is extremely complex, several overall theories are generally accepted with regard to the action of ESD. Static electricity charges on a person or object are generally like charges. As such, as static electricity charges build up on a person or object, these charges tend to migrate as far apart from each other as possible as determined by the geometry of the person of object. Thus, for example, it is common for static electricity charges to migrate to a person's fingertips. For this reason, when that person reaches out to touch an electrically conductive object, a spark will jump when the gap between that person's fingertips and the object based upon the potential difference between the fingertips and the object. This discharge is very rapid and can be quite violent. If the electrically conductive object is sensitive electronic equipment, that equipment may be damaged either from the magnitude of the discharge and/or from the speed of the discharge. At the least, the charge could cause the equipment to execute an error. A sufficient number of such discharges may eventually damage the equipment.

Accordingly, the art contains many inventions intended to protect the equipment or the person from the effects of this sudden, and sometimes violent, discharge associated with ESD.

For instance, in the logging industry where chains are lowered by helicopter to loggers waiting on the ground to fasten fresh-cut timber to them so it could be airlifted to the sawmill or nearby waterway, track access point or the like, the loggers are often reluctant to grab the chain because of a painful shock that may occur as a result of a buildup of static electricity which will be discharged to ground through their bodies. This particular problem has been solved by incorporating a resistance in the line from the charge-carrying object, such as the helicopter, to the person on the ground. The high resistance causes the current to be low enough that the discharge will not be painful.

However, this is cumbersome. This solution may be even more cumbersome if the person is an office worker who moves around a great deal. Accordingly, this solution to the ESD problem has serious shortcomings.

Accordingly, there is a need for a system that protects a person against the effects of ESD but can do so in a manner that does not interfere with any task the person may be performing and further will not be cumbersome or burdensome for the person to use.

Still other inventions are directed to protecting electronic equipment from the effects of ESD. For example, many computers include touch pads or touch areas for the user to touch before touching the remainder of the computer. The touch pads are grounded so the ESD will pass from the person via a spark or the like directly to ground without going to or through the computer.

While many of these devices work well, there are several problem areas not addressed thereby. This results in drawbacks and disadvantages for such devices when a person or equipment are situated in certain environments or subject to certain conditions.

First, no matter how effective a touch pad is it will be totally ineffective if the person does not use it. That is, if the person carrying a large ESD charge forgets to touch the touch pad and proceeds to touch a computer, the ESD will discharge through the computer and the touch pad will have been useless. Thus, a shortcoming of such touch pads is that they require the person to remember to use it.

Furthermore, no matter how effective the ESD protection device is, the current level and/or the change in current level may be so high that either the person or the equipment can be damaged.

Still further, while placing a touch pad on a computer may protect the computer it does not protect the user from the effects of an electrostatic discharge.

As mentioned above, the majority of applications for the prevention of ESD are in the manufacturing or medical fields and are largely concerned with protecting the 'manufacturing' process or sensitive components for ESD damage. Examples include moving mediums such as the manufacture of rolls of paper, the assembly of delicate electronic chips and circuitry and surgeon-patient contact during an operation.

An analysis of each of the above will help illustrate the shortcomings of the prior art. In the manufacture or printing of paper, long rolls of paper may move at high speed. Often the path may involve rubber or other rollers and guides. As the paper rubs across such items a static electricity charge may be generated. Since the paper path is well controlled, it is an easy process to place grounded conductive brushes or flat metal springs in contact with the moving paper since the paper stays in a fixed path. Such electrodes are connected directly to the grounded frame of the associated machinery or to another path eventually leading to earth ground or other equalizing means.

Another common application of ESD control is in the production or repair of fragile electronics such as computer circuit boards. Even a slight electrostatic discharge through a sensitive device may destroy it. Therefore, significant effort and cost is devoted to eliminating the possibilities of electrostatic potentials in the vicinity of the sensitive electronics. Typically, a single ground point is provided that all associated elements are connected to so that no electrostatic potential can exist between them that might flow through the sensitive electronics. For example, a conductive floor mat is provided that is connected to the ground point, or a work surface mat that is conductive (or dissipative) is also provided that is wired to the same ground point, the work table frame and any test equipment is connected to the same point, finally the assembly person is also connected to the same point, typically by a wrist strap tether. The tether generally consists of a wrist pad and grounding wire that is eventually connected back to the single ground point. For operator safety, the ground wire typically contains a 1 Meg resistor to limit current flow to safe levels should the operator come in contact with 120 volts AC. This tethering restraint is inconvenient and not considered suitable for a typical office worker or call center operator. The single ground point is eventually connected to true earth ground or other equalizing point by another conductor.

Applications are similar in the medical field, employing similar tethers and/or foot/shoe connectors also considered impractical for the typical office worker environment.

Today, a new set of ESD problems is emerging in the typical work place or home office environment. Today, a typical worker may exist in a virtually electrically isolated environment—a plastic computer case, plastic keyboard, plastic control knobs on a molded plastic control panel, plastic office chair with manmade fabric and plastic wheels, non-conductive flooring or carpeting and even a headset with foam or molded plastic earpieces and plastic microphone tube.

As the operator moves in his/her chair, there are many opportunities for a very large electrostatic charge to build up on his/her body. Friction between dissimilar materials is the classical means for generation of electrostatic voltages. There are many such situations that exist continually in the operator environment today-the operator's clothing sliding against the chair back or arm rests, the operator's shoes sliding on the carpet, the plastic chair wheels sliding against the carpet are a few examples. The effects can be cumulative over a long period of time, and can become quite high.

Eventually a discharge or equalization to (true earth) ground must take place. The higher the value of the electrostatic voltage charge, the greater the distance the charge may 'jump' to discharge, and the more 'catastrophic' the event to the operator. For example, there are many documented cases of operators in call centers experiencing a very loud pop or explosion in their ear, ear pain, and even bleeding in the ear as the discharge path appears to take place through the operator's headset. Other documented cases include severe neck pain, nausea, numbness, elevated blood pressure and rapid heart beat.

There are many possibilities as to why these effects are worse than the typical nuisance static electricity charged walking around the house. For instance, the discharge path may be more surprising or appear worse to the user if it involves the user's ear. Recently, this has been attributed to electrostatic discharge of the operator with the grounding mechanism being the metallic portion of the ear piece coupled to its metallic conductors and eventually to earth ground through its associated electronics. This may be a direct low impedance ground or it might be a higher impedance which is still sufficiently low with respect to that needed to successfully equalize the static charge. Still in other cases, as explained below, the associated electronics may potentially make the discharge injury to the person more severe and disturbing by causing a high current pulse to take place as the discharge event. This effect may be further compounded by allowing the operator to be exposed to other voltage or leakage paths developed via the ear over time.

In some cases, the associated electronics may experience physical damage or processing disturbances due to the operator electrostatic discharge. For example, the headphone circuit might involve a transformer with a 600 to 10,000 volt breakdown rating between its windings (connected to the headset diaphragm) and conductive metal core. However, the electrostatic voltage on the operator may exceed 150,000 volts-far more than the design tolerance of the transformer. Should the transformer be exposed to such excessive high voltage, a 'breakdown' or 'shorting' may occur. Thus, the operator electrostatic voltage might cause a 'short circuit' insulation breakdown or lower resistance to develop between the headset winding (secondary) and primary winding which may be at a constant high voltage level with respect to ground or the transformer core which may be connected to earth ground, thus completing the discharge path.

The transformer breakdown may cause a permanent equipment failure. Other equipment, damage or errors can also occur due to the electrostatic discharge event. The electrostatic discharge event may cause an electromagnetic or radio frequency pulse to be generated. This pulse may radiate into nearby circuitry causing errors in processing or noise in audio or video circuits. Although a transformer discharge event has been described above, other similar discharge paths can be envisioned, with similar catastrophic results.

With continued miniaturization of electronics, the problems may become more severe as circuit component voltage tolerances become less and enclosure insulation distances become less.

Accordingly, there is a need for an ESD protection system that protects a person from the effects of ESD, even if that person is in an environment that is intended to nominally insulate that person from ESD.

As the cost of doing business increases, many businesses are reluctant to purchase new original equipment. Thus, it is most advantageous if existing equipment can be easily modified or retrofit to achieve new and improved results. This is the situation with protecting people from the effects of ESD. Thus, there is a need for a system for protecting people against the effects of ESD that can easily be retrofit onto existing equipment.

OBJECTS OF THE INVENTION

It is a main object of the present invention to protect a person from the effects of ESD.

It is another object of the present invention to protect a person from the effects of ESD without requiring that person to wear any cumbersome wearing apparel.

It is another object of the present invention to protect a person from the effects of ESD without requiring the person to remember to carry out any special operation.

It is another object of the present invention to prevent or reduce an uncomfortable, disturbing or harmful electrostatic discharge to a person.

It is another object of the present invention to prevent or reduce an electrostatic discharge that might interfere with a person's ability to carry out his or her job.

It is another object of the present invention to provide a system to equalize (drain or discharge) an electrostatic charge from a person in a safe, harmless, nonnoticeable or minimally noticeable manner.

It is another object of the present invention to provide a contact surface to the person that is compatible with their normal (workspace) environment and provides discharge contact in the normal course of the operator's activities.

It is another object of the present invention to minimize the static shock that may take place upon initial contact by a prior-charged person.

It is another object of the present invention to provide a carefully controlled ground discharge path.

It is another object of the present invention to provide a ground discharge path that minimizes radiated disturbances to nearby equipment.

It is another object of the present invention to provide a discharge path that minimizes conducted disturbances to interconnected equipment.

It is another object of the present invention to provide a convenient earthing or equalization means.

It is another object of the present invention to support other work necessities of the operator such as operation of a computer mouse, keyboard, track ball or similar needs.

It is another object of the present invention to provide a grounding means via an existing ground of the associated electronics limiting the discharge current to a minimal value and waveshape so the operation of the associated electronics is not degraded.

It is another object of the present invention to provide an ESD suitable grounding means via existing signal conductors of the associated electronics limiting the discharge current to a minimal value and waveshape so the operation of the associated electronics is not degraded.

It is another object of the present invention to provide a convenient connection means for retrofit or connection in the field to existing systems by an unskilled person.

It is another object of the present invention to provide retrofit kits which can include a contact element, such as a plate, mat, faucet, handle, keyboard key, mouse, mouse pad, headset, microphone, or any of the items mentioned in this disclosure, the circuit elements mentioned in this disclosure and a connection element such as mentioned in this disclosure for connecting the assembly to ground or ESD-suitable ground.

It is another object of this present invention to define a mini version of the system of the present invention to stop or reduce nuisance shocks around houses or the workplace. For example it may mount on light switches, metal door frames, file cabinets, frames of modular office panels, front of stereo equipment or any electronic equipment where user is otherwise isolated from natural discharge paths prior to the time of contact.

It is another object of the present invention to provide a system for protecting a person against the effects of ESD using a simple plug-in jack to connect the system to any of the devices mentioned in this disclosure as a retrofit or add-on to protect a person against the effects of ESD.

It is another object of the present invention to provide a system that will be useable with a headset to protect a headset user from the effects of ESD.

It is another object of the present invention to provide a system that will be useable with a headset to protect a headset user from the effects of ESD without interfering with the operation of the headset.

It is another object of the present invention to provide a system that will protect a person from the effects of ESD and which can be releasably connected to a device that will be contacted by the user.

It is another object of the present invention to provide a system that will protect a person from the effects of ESD and which can be used in connection with an electrical plug.

SUMMARY OF THE INVENTION

These, and other, objects are achieved by a system which protects a person from ESD by reducing static charges on a person to low levels on a periodic basis as the charges are built up. Specifically, convenient, casual grounding elements are provided to periodically reduce static electric charges from building up on operators of insulated equipment in an insulated environment until a severe, often painful or harmful, static breakdown occurs in an uncontrolled manner. The system embodying the present invention provides an ESD conducting contact element which is contacted by a user on a periodic or continuous basis and often in a time extended manner of more than 0.1 second (as opposed to a simple touch) and which has a very high resistance between the contact and ground. The contact element can be a single area of a user-contacted element or the user contacted element can have several areas. The user contacted element can be in several forms, including a computer mouse, a mouse pad, headphones, a computer keyboard, a joystick, a control knob or the like. A plug or a plug connector can include a control circuit and the user-contacted element can be electrically connected to the plug or to the plug connector. As will occur to those skilled in the art, this system can be incorporated into other connections, including alligator clips, ring terminals, or the like. The plug will be disclosed only for the sake of convenience, with the understanding that the disclosure applies as well to such other connections. It is noted that for purposes of this disclosure, the word conductive will be used to refer to the electrostatic discharge contact area being discussed in the general sense unless otherwise noted. In the true sense of the ESD definition that term means all but insulators. In the strict ESD discussion, conduction typically refers to resistances of 0 to 0.1 megohm, dissipative typically refers to 0.1 megohm to about $10^{12}$ ohms, and above that as insulative or non-conductive. A combination of two or more of the following is provided: convenient personnel contact means, current limiting means, and grounding path are provided. The current limiting means may contain series elements of high resistance and/or inductance. The inductance is to limit the development of radiated or conducted high frequency, high impulse leading edges of current or voltage which may upset or damage nearby or connected electronics. The high series resistance further limits total current to a value such that static electric charges are not significant if superimposed upon logic or logic ground conductors. Geometry of the personnel contact means (such as pads or electrodes), and the series resistor values are further selected to minimize the magnitude of uncomfortable personnel static shock. The high resistance also limits current flow to the user if instead of ground the ground wire comes in contact with a high voltage source. The value of resistance can be quite high since the goal is merely to reduce the static charges to low levels (for example 500 volts or less) on a periodic basis of minutes or hours as the charge is built up. However, the large resistance prevents a person from receiving a shock if they have a charge when they initially contact the contact element. That is, the large resistance is a balance between actually connecting a contact point to a grounding circuit (which would provide a path for a walk-up shock to occur) and preventing a walkup shock by "isolating" the contact device from the grounding circuit. Points of contact to the user are designed to be those that the user touches continually or intermittently in the normal course of operation so that bleeding of ESD can occur on a continual basis. Examples may include conductive mouse pads, conductive elements on the surface of a computer mouse or computer keyboard, trackball, conductive knobs or elements on a mic mixing panel, conductive elements on the headband or earpieces of a headset worn by the user, often used controls or touch points on virtually any type or user-operated equipment. A convenient earthing means is provided to drain off the static current so the charge may be effectively equalized.

If discharge methods are not used, the static discharge might build up for minutes or hours reaching very high values. The eventual uncontrolled discharge might take place in the user's ear to the metallic diaphragm inside the earpiece. The event may be frightening to the user.

BRIEF DESCRIPTION OF THE DRAWING FIGURES

FIGS. 4a–4g illustrate segmented elements that can be touched on a periodic or continuous basis by a user and which are used in the system of the present invention.

Figure 7:
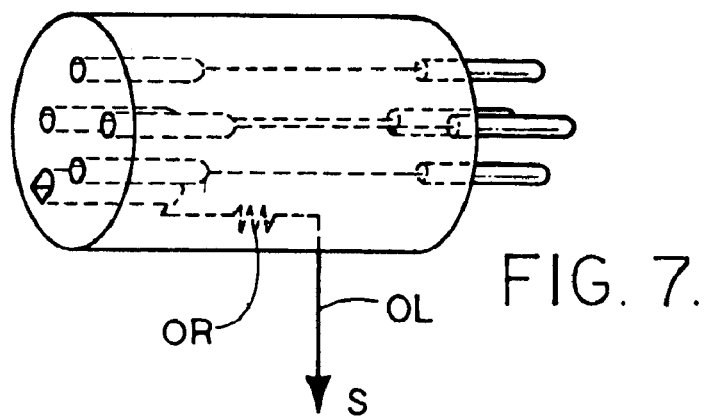

FIG. 7 illustrates an electronic device ground adapter tap that can be used in the system of the present invention. This figure shows tapping into a ground lead of an electronic device connector. The connection can be a typical RJ telephone jack or the like.

Figure 8:
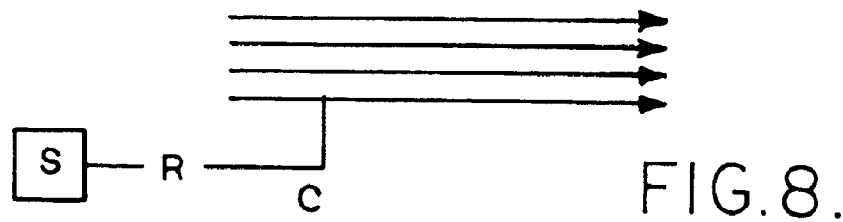

FIG. 8 is a schematic of a ground connection for use in the system of the present invention.

Figure 9:
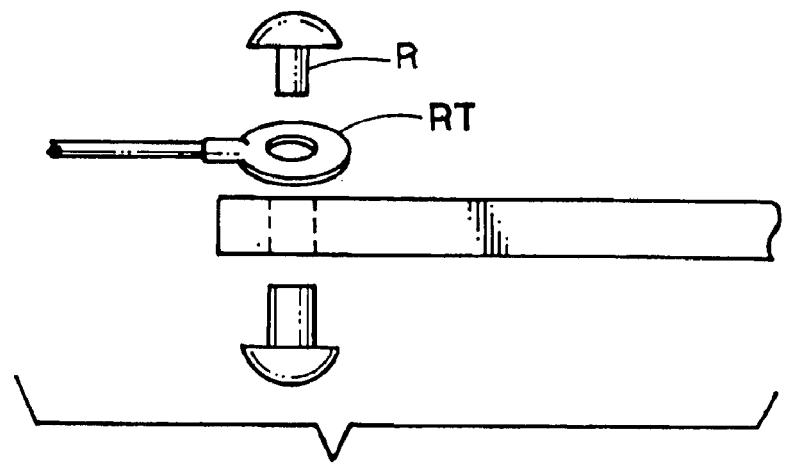

FIG. 9 illustrates a mat connection that can be used to connect a mouse pad mat to the system of the present invention.

Figure 10:
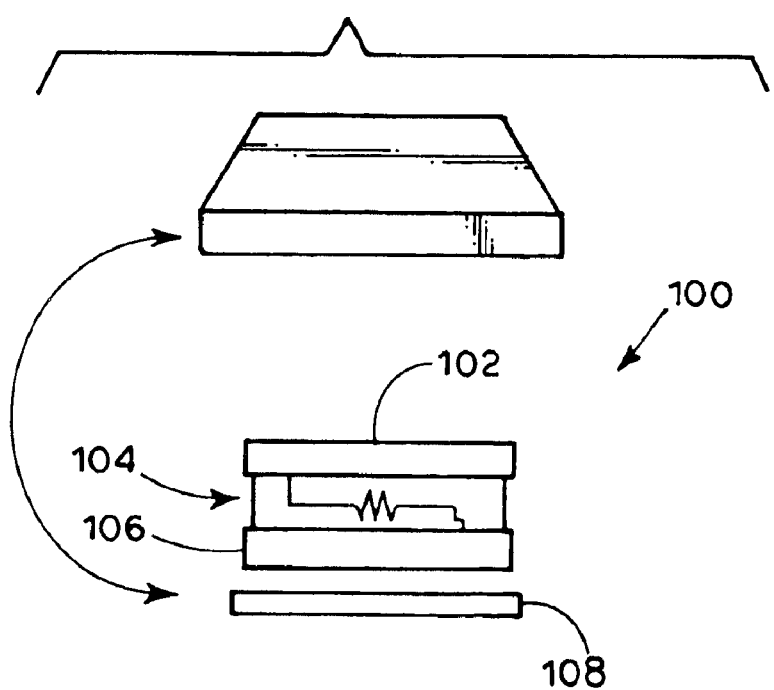

FIG. 10 illustrates a general purpose touch point that can be fixed to any equipment.

Figure 11:
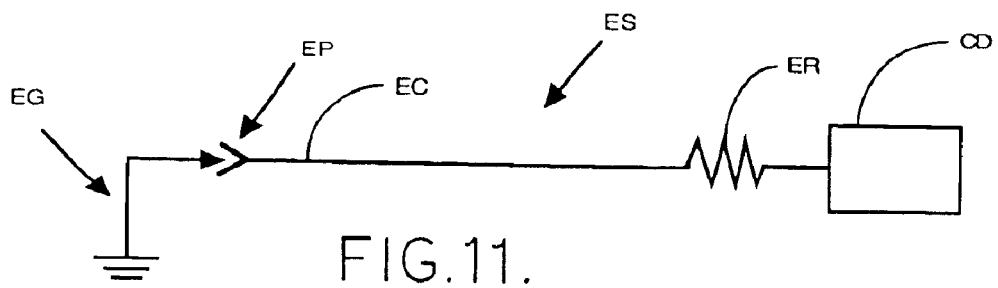

FIG. 11 is a schematic that illustrates the principle behind the present invention.

Figure 12:
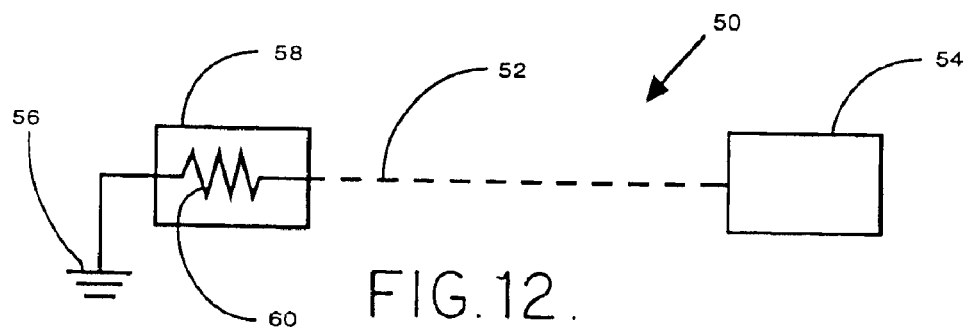

FIG. 12 illustrates another form of the system embodying the present invention.

Figure 13:
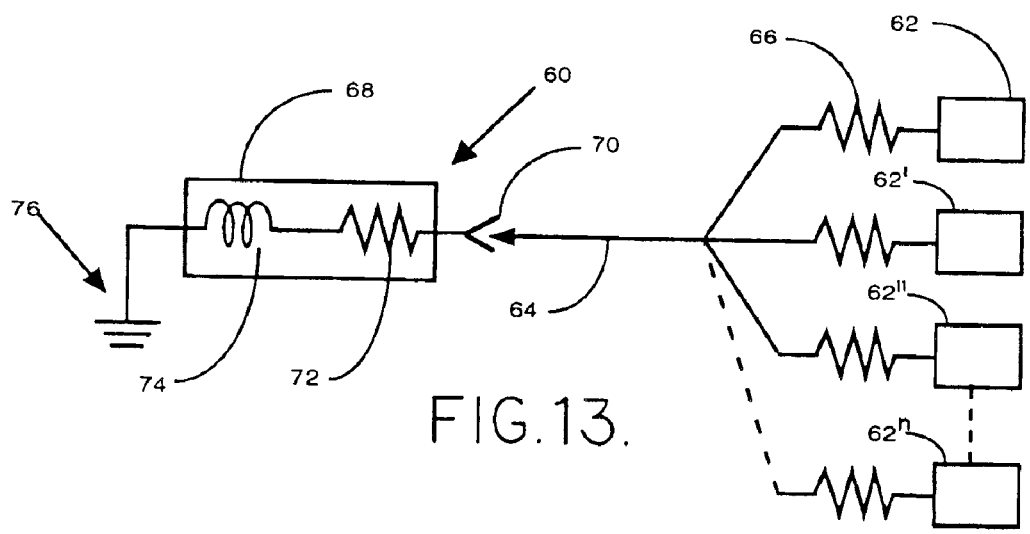

FIG. 13 illustrates the use of a plug in the system of the present invention.

DETAILED DESCRIPTION OF THE PREFERRED EMBODIMENT OF THE INVENTION

Other objects, features and advantages of the invention will become apparent from a consideration of the following detailed description and the accompanying drawings.

The build up of static charge on an individual generally takes place over time in many workplace environments. It may occur due to continued friction between shoes and carpet, clothing and chair, etc. Thus for protection it is necessary to provide a means of contact to a person's bare skin that is both casual and frequent during the work shift. Research and experience indicates that this should be every few minutes or so. Most individuals do not feel a discharge shock of 2000 volts or less and experience indicates that voltages may be building to the 5000 volt, 10,000 volt or more range before breakdown occurs. Generally, the operator is at his/her work position for an hour or more before the breakdown occurs.

Such breakdown may be considered as potentially disturbing to both the person and equipment, far more so than the typical nuisance discharge experienced when walking across a carpeted floor in the winter and touching a door knob. For example, there are cases of shock experienced when reaching for the "mute" button on an operator's telephone or from the user's ear through the metal parts of a headset worn by the operator.

There are many documented cases of this last occurrence requiring paramedic medic attention for weakness, blurred vision, high blood pressure, increased heartbeat, etc. There appears to be two reasons why this is more severe than the typical doorknob shock: (1) the electrostatic buildup may take place for a long time before breakdown occurs and hence be of greater magnitude than the typical carpet charge; (2) if discharge occurs at the ear, the associated sound may appear very loud to the operator, further adding to the perceived severity of the shock.

Generally the minimum discharge voltage a person can perceive is about 2000 volts. For purposes of this discussion an electrostatic voltage of 10,000 volts is assumed as a walk up initial voltage when first touching the ESD protective mat and is the voltage that will be used in the following discussion.

In many workplace applications historically metal grounded surfaces have been used so a zero resistance to ground is common and considered safe. However, the initial walk up discharge shock in such a case can be very significant and disturbing. The shock is significant because significant electron flow takes place due to the obviously large number of electrons available in the earth for neutralization. A similar shock also takes place when touching large metal objects because of the large number of electrons available in the object for discharge. This inventions limits the initial electron flow in two ways:

The discharge current is minimized by the resistance R of the control circuit and inherent resistance of the mat. A resistance of approximately 10 meg ohms or greater has been determined to be sufficient to minimize these initial shock effects.

By segmenting or minimizing the size of the conductive surface the number of electrons in its contribution to the initial shock are also reduced. For example, experimentation with conductive vinyl mats indicates surfaces of 1–2 square feet exhibit much less shock perception than mats of 5 square feet.

This principle can be understood by referring to FIG. 11. A system ES is shown that includes a contact element, such as a mat EM that is electrically connected to a ground circuit EG by plugging a conductor EC into a grounded connection GC at plug EP. Grounded connection GC is directly connected to earth which contains a large mass of electrons. The conductor EC, itself, is a source of electrons. Thus, if a person who has built up an ESD charge touches conductor EC, the mass of electrons in the ground and in the earth will be available for a shock to that person. A contact device CD is shown and can be a mat or any other object that is likely to be touched by a user. If device CD is isolated from any mass of electrons, the person touching that device will not receive a shock. However, if there is any mass of electrons available, even if the mass is associated only with conductor EC, the person is likely to receive a shock upon touching device CD. However, if device CD is not electrically connected to some mass of electrons, the person touching device CD will not discharge the electrostatic energy he or she has built up. Therefore, there is a double-edge sword present: there must be some mass of electrons available so a discharge can be effected; however, the mass of electrons must not be so large that a painful shock is felt upon the discharge occurring.

Realizing this, the present invention electrically connects a contact device to a source of electrons, but does so in a manner that keeps the mass of electrons available to a minimum. The invention achieves this result by placing a resistor, such as resistor ER, physically close to the contact point so some electron mass is available, but not a large electron mass as might be present if the wire itself is present in the discharge circuit. Heretofore, no one has realized that the wire itself might be a source of electrons that produce a shock during ESD. The resistor being physically close, in some cases, within one foot, to the contact point reduces the mass of electrons available to discharge the electrostatic charge on a person. Since the mass of electrons is reduced, the discharge will be slower than if a large mass of electrons is available. Thus, the present invention accounts for this by creating a situation where the person contacts the discharge contact on a continuous basis for long periods of time (long with reference to a touch, that is, longer than a touch). The "slow" slight discharge is nearly, if not totally, unnoticed by the person; yet is extremely effective in achieving the ultimate purpose of bleeding the ESD from a person in a non-noticeable manner.

The above concepts can also be applied within devices like headset assemblies to reduce initial shock and random shock from moisture build up on the earpiece.

Figure 1:
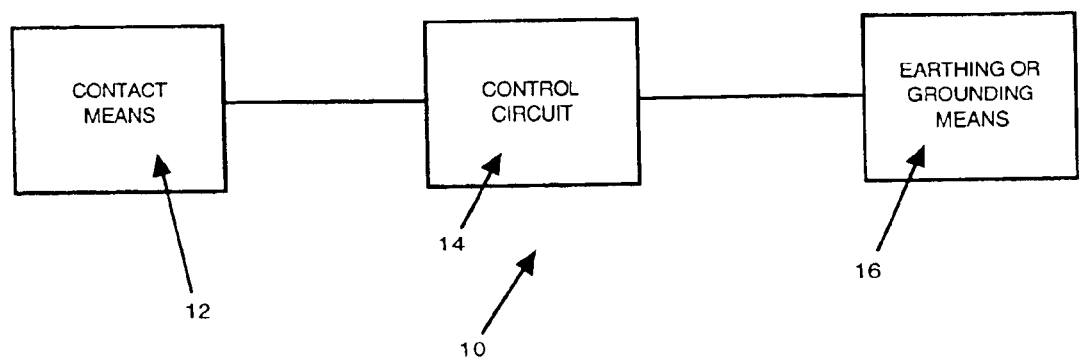
FIG. 1 is a block diagram illustrating the broad system for protecting a person from the effects of ESD as embodied in the present invention.

Specifically, referring to FIG. 1, it can be seen that the system 10 for protecting a person from electrostatic discharge includes an ESD conducting contact element 12 electrically connected to a control circuit 14 which is electrically connected to earth 16.

Contact element 12 can include one or more surfaces that come in contact with the operator's skin. These surfaces may be metal, or various compounds representing electrical conductivities from zero to approximately 15 Meg ohms. They may have other properties as needed for a specific work application such as a hard surface to support writing or the hardness and smoothness to support use of a computer mouse.

Figure 2A:
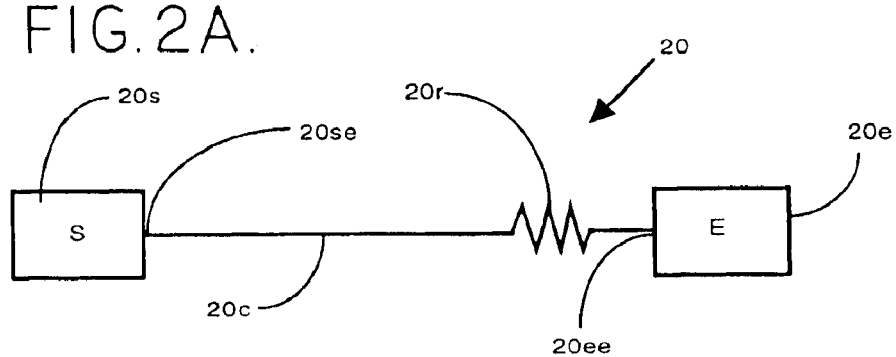
FIGS. 2a–2h illustrate circuits that are used in the system of the present invention.

The particular circuits that can be used in control circuit 14 are shown in FIGS. 2a–2g. As shown in FIG. 2a, circuit 20 includes a conductor 20c electrically connected at one end 20se thereof to the contact element 20s, such as a custom computer mouse mat, or the like, which is contacted by the user, and at the other end 20ee thereof to earth 20e. A resistor 20R is placed in conductor 20c near end 20ee. As discussed above, if this resistor is used as the sole resistor that isolates the touch contact element from ground, resistor 20R can have a resistance of approximately ten megohms and can be as high as greater than sixty megohms. Resistor 20R can also be selected to provide minimum safety requirements should the ground be faulty or contact be made with 120 volts, and is typically 1 meg ohm or higher to limit the maximum discharge current to a safe value.

Figure 2B:
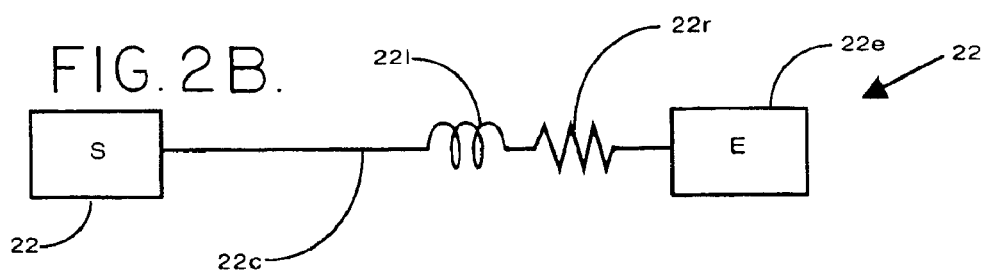

Circuit 22 shown in FIG. 2b includes an inductor 22L which reduces radio frequency interference traveling back to nearby equipment such as a PC where it might disrupt the system. Typical values for inductor 22L are in the range of 2 to 1 millihenry. The value may be chosen based on circuit, financial and space restraints. Circuit 22 otherwise includes elements that are similar to the above-discussed elements for circuit 20, and thus includes a conductor 22c connecting contact element 22s to earth 22E.

It is noted that the resistors in circuits 20 and 22 are located near the earthing or grounding system as opposed to near the contact location. Such circuits are used in the situations where the contact elements are insulative-type elements in which a large mass of electrons will not be present so a walk-up shock is not likely. Thus, such insulative contact elements need not be "isolated" by a resistor located physically close to the contact element as will be understood from the foregoing discussion.

Figure 2C:
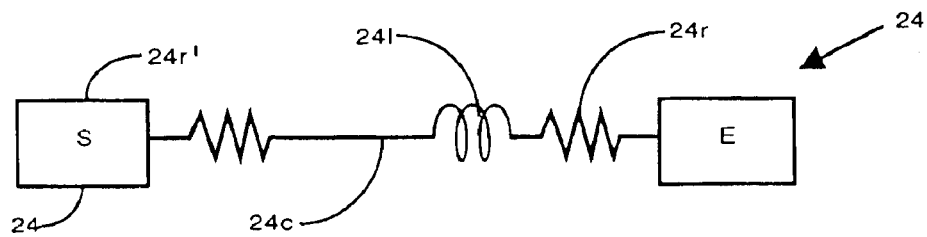

Circuit 24 shown in FIG. 2c further includes a second resistor 24R' located near contact element 24s to reduce the effective number of electrons from the wire and ground immediately available to neutralize a user's charge. This eliminates or reduces the wire itself and the eventual earthing from contributing to the initial walk-up shock or subsequent shock by a static-charged user upon making contact with the contact element.

Figure 2D:
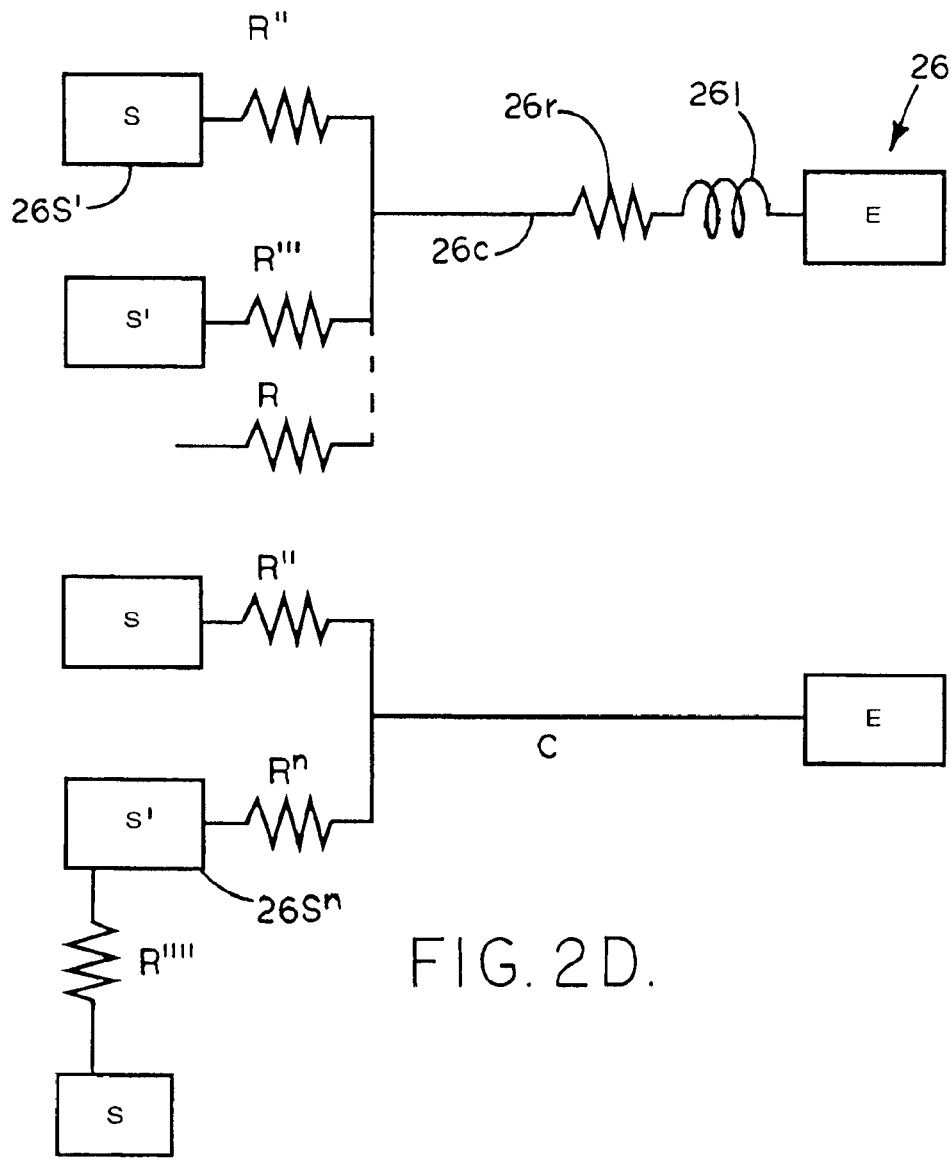

Circuit 26 shown in FIG. 2d is used in connection with multiple contact elements or surfaces 26s' . . . 26s'' and all such elements include a resistor, such as resistor 26R' . . . 26R'', each of which is connected to conductor 26c which has a resistor 26R and can include an inductor 26L as well connected to ground element 26E. Resistors 26s reduce the number of electrons immediately available at each individual contact element or contact surface to neutralize a user charge.

Figure 2E:
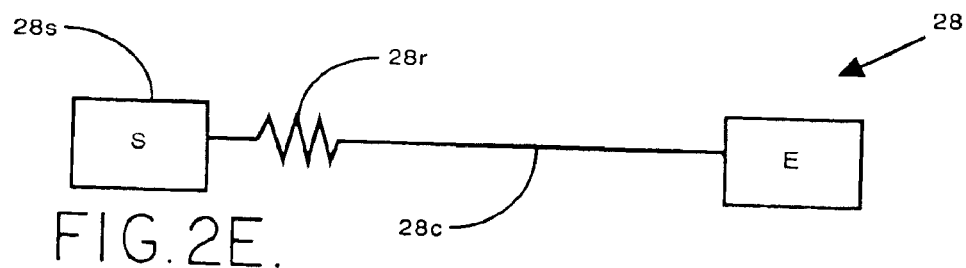

Circuit 28 is shown in FIG. 2e and includes a resistor 28R located in conductor 28c adjacent to contact element 28S.

Figure 2F:
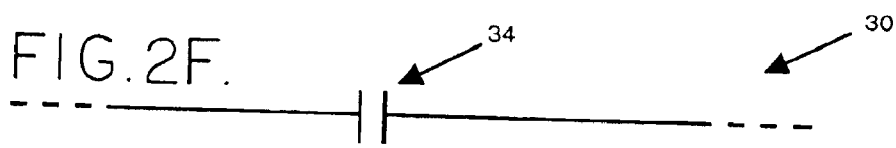
Figure 2G:
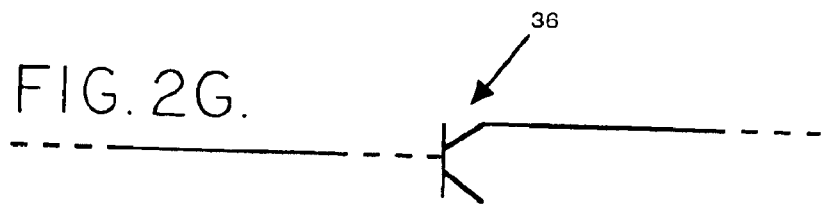

It is also noted that additional circuit elements can be included in conductor c as performance demands. Thus, as shown in FIG. 2f, circuit 30 includes a capacitor 32 while circuit 34 in FIG. 2g includes a transistor 36. Both of these circuit elements are in addition to the above-discussed resistors and inductors.

Figure 2H:
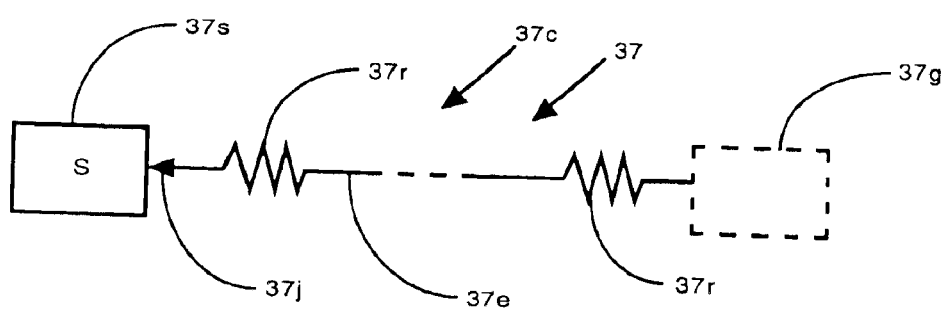

FIG. 2h shows a system 37 for protecting a person from surprise or uncomfortable electrostatic discharge (ESD) and which comprises: an electrostatic discharge conducting contact element 37S which is in time-extended contact with a person who is to be protected from electrostatic discharge when in use; a control circuit 37C electrically connected to contact element 37S by a conductor 37e. The control circuit includes a first resistor element 37R which is in series with the contact element and which has a resistance which will drain some, but not all, ESD from contact element 37S. The system further includes a ground circuit 37G which is electrically associated with control circuit 37C either by electrical conductors or by over-the-air signals such as radio signals. Resistor 37R is physically located near contact element 37S, such as within one foot thereof. Resistor 37R can have a value that ranges from as low as one megohm to as high as more than one hundred megohms. As shown in FIG. 2h, circuit 37C further includes a second resistor 37R' that is located physically close to ground circuit 37G to prevent shock associated with an improperly grounded circuit, and can have a value in the range of one megohm.

As shown in FIG. 2h, a jack connector 37j can be used to electrically connect circuit 37C to contact element 37S. Thus, if contact element 37S is a computer element, such as a keyboard, logic circuit, mouse, mouse pad or the like, circuit 37C can be releasably connected thereto using jack 37j. As will be understood from this disclosure, any of the circuits shown herein can be releasably connected to a contact element using a jack. Thus, while a jack may not be specifically shown in each figure, it is to be understood that such a releasable connection can be used between the circuit and the contact element. The specific showing is not presented in all figures for the sake of convenience.

It is noted that R and/or L as above also permit the grounding path to be via grounding conductors present in most electronic equipment or even logic conductors as applicable for the particular equipment. For example, consider an electrostatic voltage of 10,000 volts and R of 40 Megs. The resultant maximum current is 0.25 ma which could safely be inserted on most grounds or applicable logic or signal conductors without adverse effects, especially with L if needed to further reduce the maximum initial current and high frequency components. Typically the on-going voltage incrementally generated by the operator is in the 100s of volts, resulting in virtually minor microamps of ground or signal currents. These would typically be of no concern in most properly designed electronics.

The high value of R also permits flexibility in use of mat materials. For example vinyl conductive mats ESD mats typically have resistances of 100,000 ohms, not enough to meet the needs discussed here. However they have the advantages of low cost, long life, easily cleaned, allergy-free, and capable of being written or used with a mouse. The high values of R discussed herein make them suitable for the applications discussed.

Figure 3A:
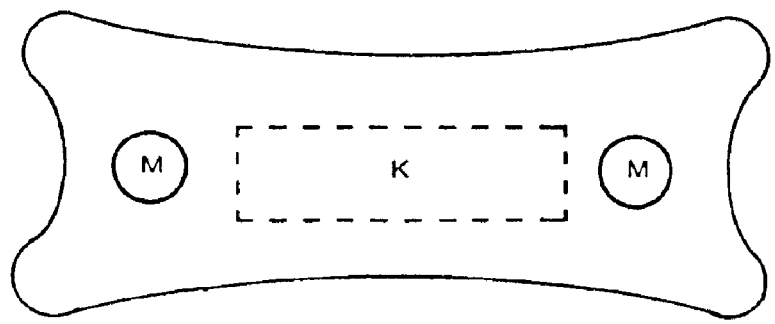
FIGS. 3a–3l illustrate elements that can be used in the system for protecting a person from the effects of ESD these elements are contacted on a periodic or continuous basis by the user during his or her work.
Figure 3B:
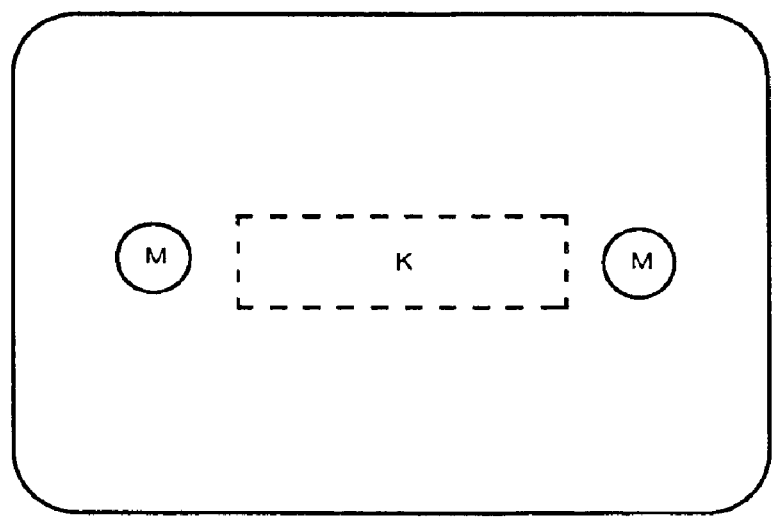
Figure 3C:
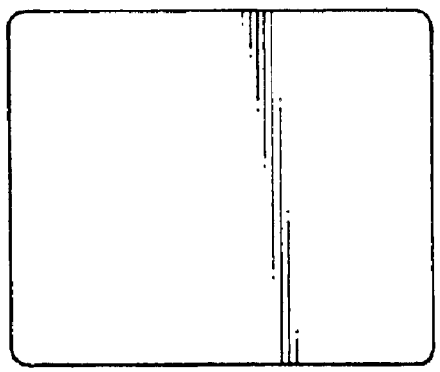
Figure 3D:
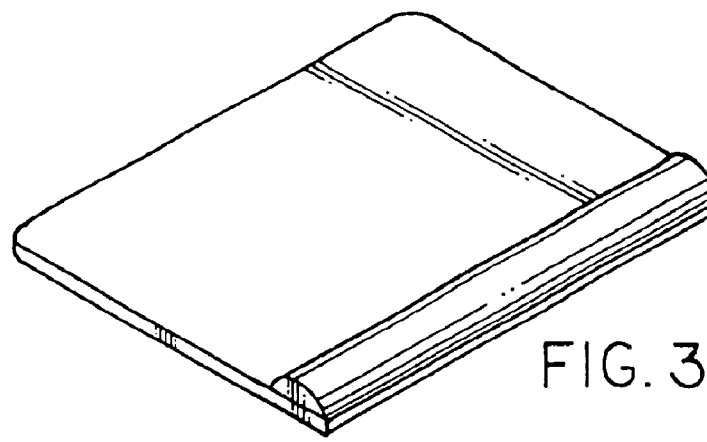
Figure 3E:
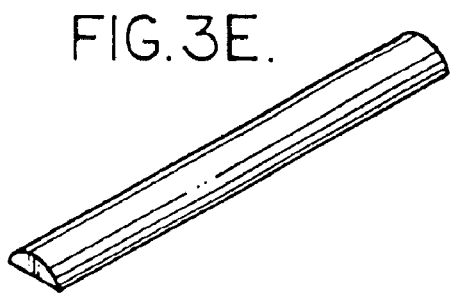
Figure 3F:
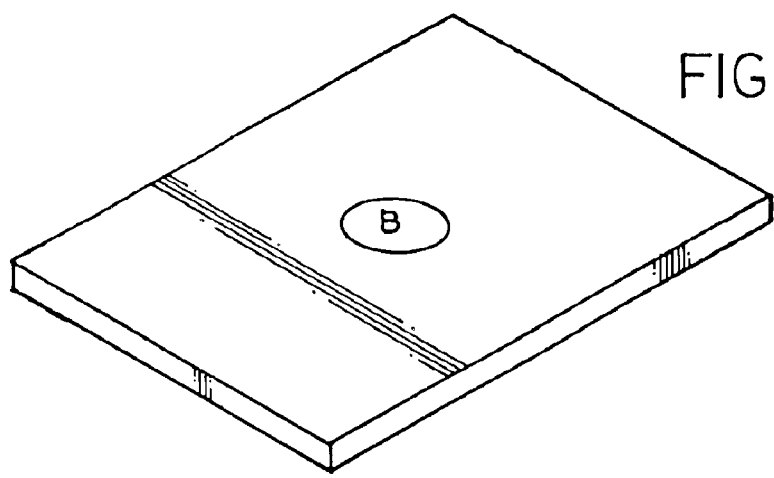
Figure 3G:
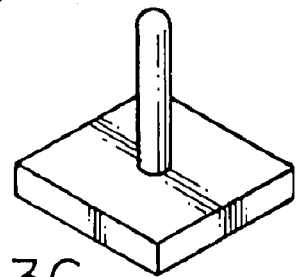
Figure 3H:
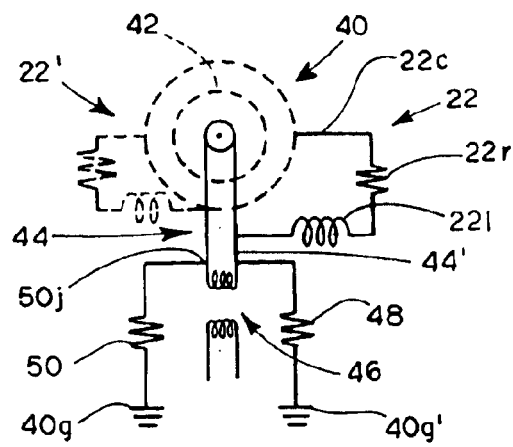
Figure 3H:
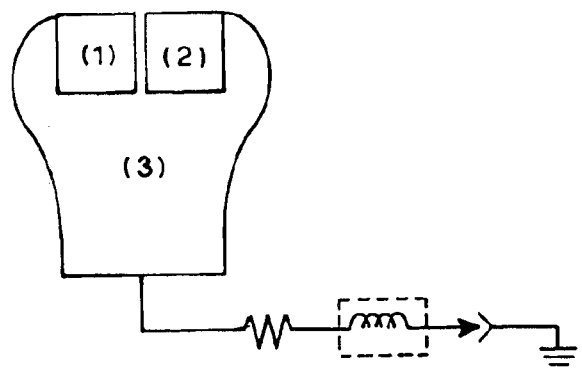
Figure 3I:
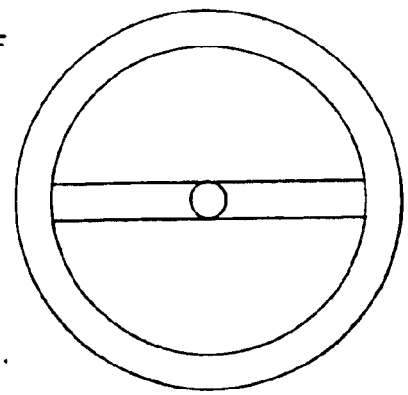
Figure 3J:
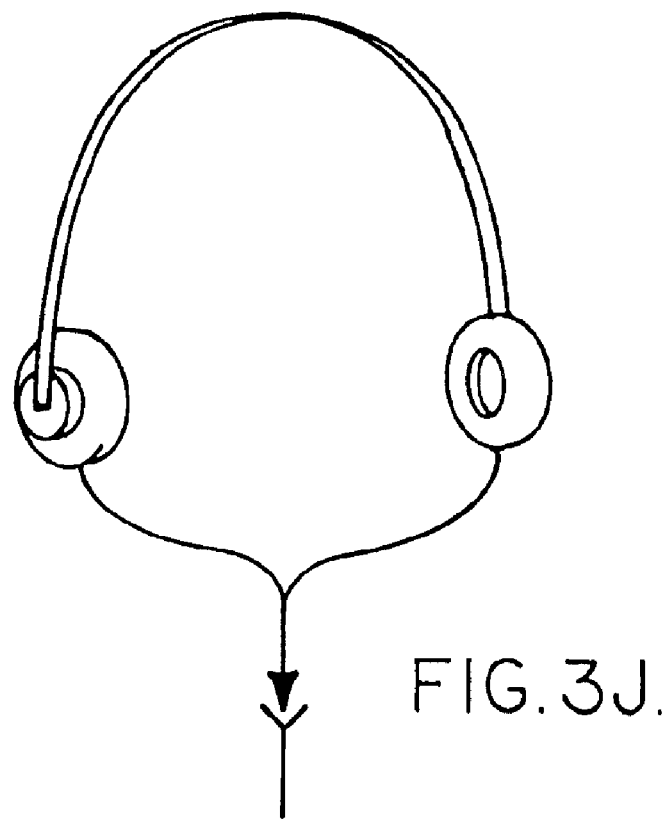
Figure 3K:
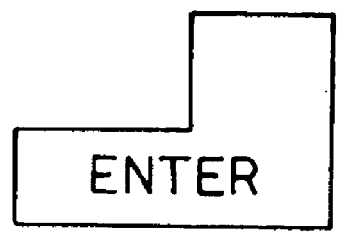

FIGS. 3a–3k1 illustrates various connections to the operator or individual where ESD protection is desired. FIG. 3a illustrates one configuration of a custom electrostatic contact mat. Other similar configurations will occur to those skilled in the art based on the teaching of the present disclosure. This configuration completely covers a work surface shape common in modular furniture used in call centers. The out line covers the entire work surface for esthetic purposes. A typical computer keyboard (K) can sit in the center of the mat while allowing space on either side for a computer mouse (M) or similar device. The surface of the mat may be suitable hardness and smoothness for operation of the mouse or other workplace needs. The electrical resistance of the mat is selected in conjunction with the control circuit for desired operation characteristics.

Figure 3L:
Figure 3M:

FIG. 3b is a similar mat of smaller size still permitting mouse operation on each side of the keyboard. FIG. 3c is a smaller configuration similar to a typical mouse pad. FIG. 3d is a wrist pad in combination with a mouse pad. FIG. 3e is a separate wrist pad which may be configured to fit next to or upon a mouse pad, may be configured in conjunction with a key board or for other general purpose use in the work place. FIG. 3f is a trackball configuration where the either or both the trackball and surrounding pad may be used the conducting means. FIG. 3g is a configuration of a joystick design where the handle and/or rest area can be conductive. FIG. 3h is a typical computer mouse where all or part of the body such as the click pads, or the like may be conductive. FIG. 3i is a steering wheel or cockpit stick where all or part of the structure may be conductive. FIG. 3j is a typical headset apparatus which may include many points of conductivity including but not limited to: the headband, the ear pad(s) via a direct earthing connection, the ear pads via the metal diaphragm of the earpiece, a special grounding conductor relating to part of the headset such as but not limited to the headset band, earpads, microphone, quick disconnect coupler, etc. FIG. 3k is a configuration of a key on a keyboard, such as the ENTER key. Other commonly used keys such as the space bar or the home keys may be used. Or, all or a portion of the framing of the keyboard such as the palm rest area may be used as a conductive surface. This may be by selection of the materials used for construction, application of conductive materials such as paints, etc. FIG. 3l is a control button, such as the mute button on a telephone or headset control, control knob or other selected surface on any electronic or workplace instrumentation. FIG. 3m is a configuration of a dedicated 'touch point'. This may take many convenient forms, such as a small bumper, a design or a logo. Other such designs to permit frequent casual contact between a person and ESD protective surface will be understood by those skilled in the art based on the disclosure herein.

FIG. 3k1 shows a headset connection with a circuit, such as circuit 22, included. As can be seen in FIG. 3k1, headset 40 includes an earpad 42 and an earphone circuit 44 which includes a transformer 46. As shown in FIG. 3k1, circuit 22 includes a conductor 22c connected at one end thereof to earpad 42 and at the other end thereof to circuit 44 and a resistor 22R and an inductor 22L are also included as discussed above. The inductor can be optional. It is noted that any of the circuits shown in FIG. 2 can be used without departing from the scope of this disclosure and circuit 22 is shown simply for the sake of convenience. Further grounding resistors 48 and 50 can also be included as shown in FIG. 3k1. Typical values of Resistors 48 and 50 may be 10–60 megs. They should be high enough not to disturb normal operation of the signal circuit, typically 600 ohms, but low enough to drain ESD. Resistors 48 and 50 and the ground connection may be mounted in an adapter assembly which can be a separate item. There may also be cases where circuit 22 need not be separate from the headpiece. Such situations occur when the foam in the headset is such that circuit 22 is really part of resistors 48 and 50.

In practice, the purpose of circuit 22 as shown in FIG. 3k1 is to allow the (ESD) conductive piece in contact with the ear to become part of a similar ESD controlled circuit as described herein. In some physical cases of construction the conductive elements such as earpiece 40 and pad 42 or other elements as described earlier such as the headband, etc may make other acceptable contact with conductors 44 and 44'. These items are located in the headset. Transformer 46, or another headset-driving circuit, may be located elsewhere as in a headset amplifier box or telephone. The headset to amplifier box/telephone connection is usually connectorized at one or more points by adding jacks or the like where circuit 22 can be removably connected to the headset. Thus the resistors 48 and 50 plus elements as needed of circuit 22 may physically be located in a separate connectorized adapter assembly as a retrofit or designed product. The ground connections 40G and 40G' may be connected to the plug or adapter assemblies of FIGS. 5, 6, 7, or 8. In practice, resistors 48 and 50 will generally be of the same high values to maintain the signal line as balanced and higher in value so as not to disturb the line for a signal standpoint. It is observed that, in the example shown, resistors 48 and 50 are in parallel and then in series with the remainder of circuit 22. Thus the value of resistor 48 and resistor 49R may be considered as components in achieving the circuits of FIG. 2. Likewise the capacitor variations of FIG. 2 may be added to maintain direct current or low frequency characteristics of the original signal circuit. In some cases only Resistor 48 may be required. As is also shown in FIG. 3k1, two control circuits, 22 and 22' can be used with control circuit 22 being connected to line 44' and control circuit 22' being connected to line 44. This will provide a balanced pair circuit. Circuit 22' is identical to circuit 22 and thus will not be further discussed. Furthermore, the ground resistors, 48 and 50 can be releasably connected to lines 44 and 44' by jacks or the like as indicated by jack 50J in FIG. 3k1. This will permit the resistors to be connected as needed. It is observed that resistors 48 and 50 have values that are high enough to drain ESD and so high as to not interfere with operation of the earphone circuit. Values of resistors 48 and 50 are of the range of the insulation commonly used on headset wires such as wires 44 and 44'. Other variations will be obvious to those skilled in the art based on the teaching of the present disclosure.

Figure 4D:
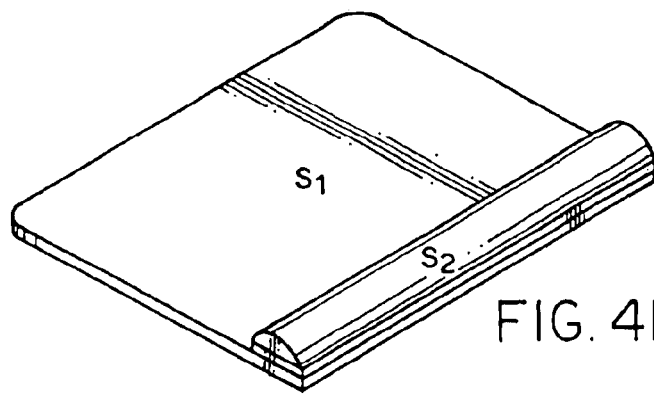

FIGS. 4a–4g show designs similar to FIG. 3 in overall size and appearance, but cut into electrically isolated sections. For example, FIG. 4a is the same mat as FIG. 3a but cut into three electrically isolated sections. FIG. 4b is FIG.

Figure 4E:
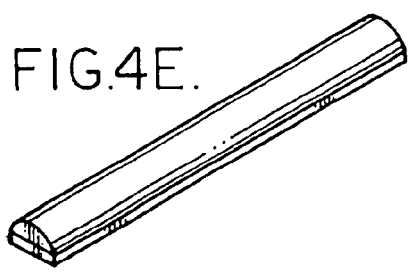
Figure 4F:
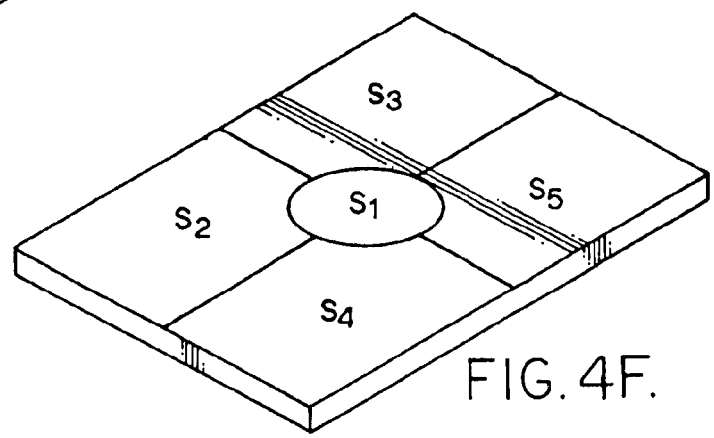
Figure 4G:
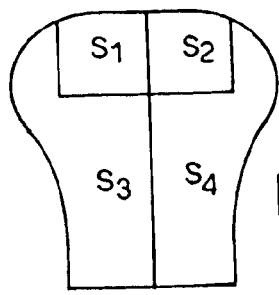

3b cut into two sections. FIG. 4c1 is the same as FIG. 3c but with a small piece (S2) electrically isolated. FIG. 4c2 has the touchpoint of FIG. 3h applied to a portion of the original mat. FIG. 3d has the wrist support section cut and isolated from the main body of the mat. FIG. 4e has the wrist mat pad cut and isolated into two sections. FIG. 4f contains the trackball itself as an isolated item and pad cut for a total of five isolated surfaces. Other such geometries will occur to those skilled in the art based on the teaching of this disclosure.

Figure 5A:
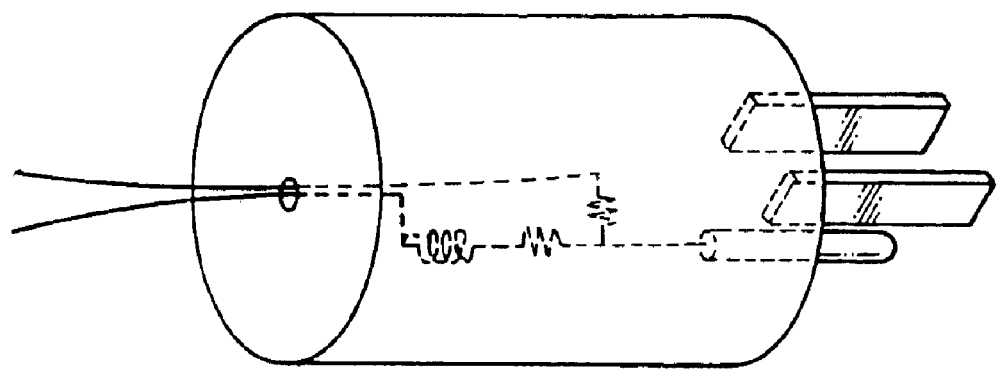
FIGS. 5a–5e illustrate a plug that can be used with the system of the present invention.
Figure 5B:
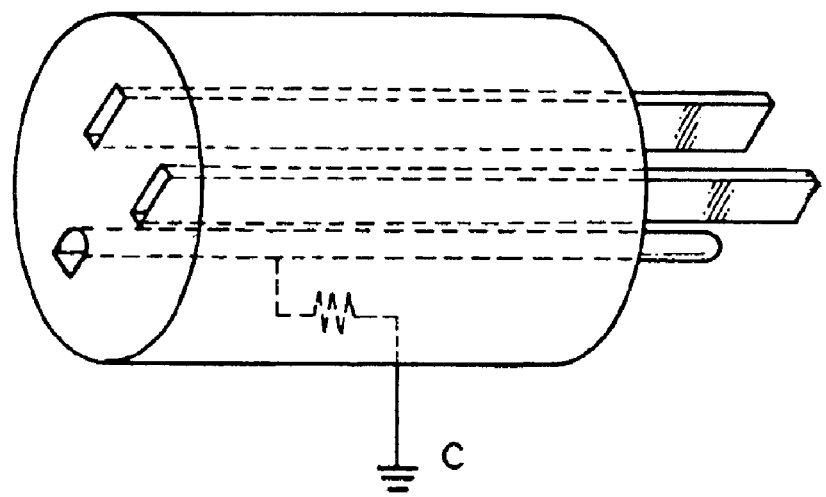

FIGS. 5a–5d illustrate a plug that can be used to house all or a portion of the control circuit of the present invention. FIG. 5a shows use of a standard configuration electrical plug for grounding purposes, corresponding to the earthing/grounding portion of the system in FIG. 1. The plug may contain circuitry elements from FIG. 2, including additional grounding conductors for other purposes such as wrist straps, headset adapter grounding, carpet adapter grounding or additional surface segments. The normal conducting phase and neutral prongs are not used except for mechanical stability. They may be replaced by one or more non-conducting materials such as being molded with the body of the plug or eliminated. FIG. 5b shows an in-line adapter assembly incorporating male and female plug/receptacle elements, external grounding conductor (c) and/or circuitry of FIG. 2. This adapter does not displace a plug from being connected in situations where there is not a spare receptacle position and also provides a useful ground connection where none may be available, such as modular furniture arrangements where the is no exposed center ground screw in the receptacle. It is noted that this the opposite of appliance adapters sold for older homes which do not have a grounding receptacle and require a separate grounding conductor to furnish ground and physically accommodate a grounded appliance plug.

Figure 5C:
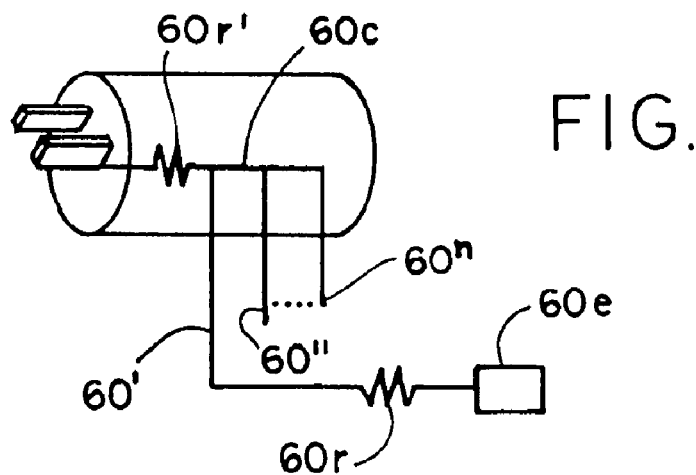
Figure 5D:
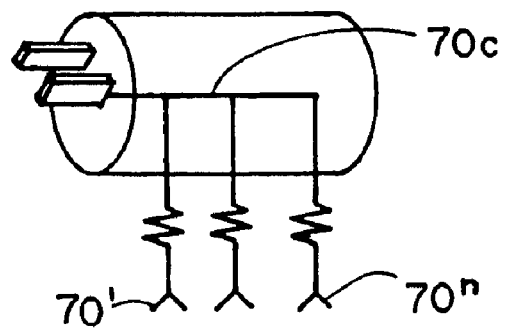
Figure 5E:
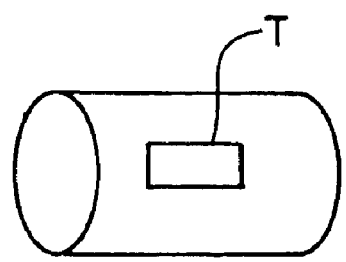

FIG. 5c shows another form of the circuit in the plug with a plurality of connections $60'$ ... $60^n$ to the main conductor $60c$ which includes a resistor $60R'$ therein and has a resistor $60R$ located near earthing $60e$. FIG. 5d shows another variation of this circuit with resistors $70'$ ... $70^n$ connecting plugs $72'$ ... $72^n$ to conductor $70c$, and FIG. 5e shows a plug having a test circuit T therein. Test circuit T can be used with any of the plugs discussed herein to be sure there is a proper circuit connection made by the plug. For example, the test circuit can be used to verify the correct polarities, especially the ground circuit polarities, and to verify that the ground circuit is truly grounded and conductive. As can also be seen, especially in FIGS. 5b–5d, the plug need contain only a portion of the overall circuit, with the remainder of the circuit being located outside the plug. This will permit the plug to be a part of an overall circuit. However, the entire circuit can be contained in the plug if desired so the plug can be sold as an entity in, and of, itself.

Figure 6:
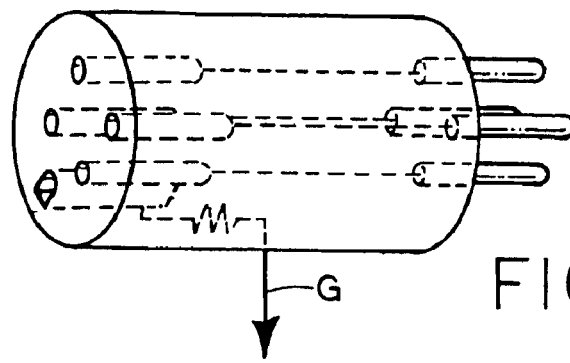
FIG. 6 illustrates an adapter device that can be used with the system of the present invention.

FIG. 6 shows an example of a plug that is used with receptacles that do not have a specific ground connected suitable for the ESD function described herein. This plug/adapter is an adapter allowing a grounding conductor to be tapped off from an instrumentation plug or assembly. For example, the adapter may have the output (pin) configuration of a standard mouse or microphone connector, thus fitting such standard female connectors. The female side may contain an extra pin for connecting the circuit to an ESD protective surface or surfaces as shown in FIGS. 3 and 4. Thus a single cable could be used as today from a mouse but it could contain grounding servicing an ESD conductive surface on the mouse. Conductor G is subsequently grounded. The female pins are configured as a standard configuration for example standard mouse plug, or the like, for compatibility purposes.

FIG. 7 is an adapter containing equivalent male/female connectors so that it may be connected in line to a mouse, keyboard, microphone or other electronic connectors. An output lead OL is subsequently connected to an ESD protective surface or surfaces as discussed above with a resistor OR serving the purpose discussed above. Output lead OL may be connected to an existing ground lead in the adapter or even a signal or voltage conductor depending upon circuit parameters.

FIG. 8 indicates the connection of an ESD protective surface (S) directly into ground or logic signals already present in the assembly. For example, S might be the surface of a mouse treated to be conductive or dissipative and the network R connects into an existing ground or logic connector within the mouse so compatibility is maintained with standard plug-ins thus allowing an ESD protective mouse to be plugged into standard mouse receptacles on existing computers. Other similar arrangements on other electronics will be obvious to one skilled in the art, including alarms, control circuitry, studio equipment, and the like.

FIG. 9 indicates an inexpensive method of connecting to the ESD mat instead of the snap method commonly used. A rivet R fits through a ring terminal RT to be connected to the mat. Lower cost, smaller size and better connection are advantages.

FIG. 10 illustrates a touch configuration 100 for easy application to grounded surfaces. The purpose is to eliminate the typical nuisance static shock which happens from touching a grounded or large metal object. Touch configuration 100 includes a top surface 102 of metal, conductive means or dissipative means connected to a second surface or circuit 104 of desired performance properties which may be connected to another optional metal or conductive means 106 which may then be connected to another optional mounting means 108 such as a conductive adhesive. Thus the entire assembly becomes an electrostatic dissipation applique of particular performance which may be applied to a wide variety of applications. It may be configured so that a screw or other mounting means may be used in place of the adhesive.

FIG. 12 shows an alternative form of the system embodying the present invention. System 50 shown in FIG. 12 utilizes the concept discussed above that a reduction in the mass of electrons available will reduce the degree of shock received by someone touching a contact device when he or she is carrying an electrostatic charge yet a small mass of electrons is necessary to effect the discharge of that electrostatic charge. Thus, system 50 uses a very thin wire 52, such as a Litz wire, having the outer diameter approximately equal to the outer diameter of a human hair, to connect contact device 54 to a ground circuit 56. A plug 58 is used to connect wire 52 to ground circuit 56. Plug 58 has a resistor 60 which is sized to reduce the ground electron mass and can be ten meg ohm or greater.

A further form of the system is shown as system 60 in FIG. 13. System 60 is associated with a segmented mat or other system in which there are a plurality of touch points. The separated touch points are shown in FIG. 13 as including Contact elements $62$ ... $62^n$ which are each electrically connected to conductor 64 by a resistor such as resistor 66 that is located physically close to the contact point to limit the size of the mass of electrons "seen" by the contact element. The resistors 66 are the same size as the first resistors discussed above, such as resistor 20R, and can be ten meg ohm or more if suitable. These resistors are then electrically connected to a plug 68 by conductor 64 via a releasable plug 70 that can be a plug that permits several plugs to be ganged together. Plug 68 includes a resistor 72 which is one meg ohm or greater for the reasons discussed above. An inductor 74 can also be included if suitable. The size of the inductor was discussed above. Plug 68 is electrically associated with a ground circuit 76.

As can be understood from the foregoing, the method embodying the present invention protects a person from surprise or uncomfortable electrostatic discharge (ESD) and comprises: providing an electrostatic discharge (ESD) conducting contact element; initially contacting the ESD contact element for a time-extended period of longer than a touch; and draining some, but not all, ESD during the initial contact. As was also discussed above, the person contacting the contact element is protected from shocks due to a grounding error, and the method is set up to drain small amounts of ESD at each touch, which amounts are small enough that the person is not made unreasonably uncomfortable by the discharge of electrostatic energy at each touch, including the initial touch. The repeated and/or time extended nature of each touch permits the draining of ESD in small amounts over extended periods of each touch to achieve this result.

It is understood that while certain forms of the present invention have been illustrated and described herein, it is not to be limited to the specific forms or arrangements of parts described and shown.

What is claimed is:

1. A system for protecting a person or equipment from surprise, damaging or uncomfortable electrostatic discharge (ESD) comprising:
   a ground system having stray inductance and resistance;
   a plurality of devices electrically connected to said ground system;
   an electrostatic discharge contact element on at least one device of said plurality of devices;
   a resistor element electrically connected to said contact element; and
   an inductor element electrically interposed between said contact element and said ground system and which is connected to said ground system at a connection location.

2. The system defined in claim 1 wherein said resistor element is physically located closely adjacent to said contact element and is in series with said inductor element.

3. The system defined in claim 2 further including a second resistor element in series with said inductor element.

4. The system defined in claim 3 wherein said inductor element is physically located between said resistor element and said second resistor element and said resistor element is physically located between said contact element and said inductor element.

5. The system defined in claim 2 wherein said resistor element is located within one foot of said contact element.

6. The system defined in claim 1 further including a second resistor element, and said second resistor element having a value of at least one megohm and is in series with said inductor element.

7. The system defined in claim 1 further including a capacitor in series with said resistor element.

8. The system defined in claim 1 further including a transistor in series with said resistor element.

9. The system defined in claim 1 further including a second electrostatic discharge contact element.

10. The system defined in claim 1 further including a user contactable element and said electrostatic discharge contact element is located in said user element.

11. The system defined in claim 10 wherein said user contactable element includes a computer mouse pad.

12. The system defined in claim 1 wherein said resistor element has a value of approximately sixty megohms.

13. The system defined in claim 1 wherein said ground circuit includes signal leads.

14. The system defined in claim 1 further including a conductor electrically connecting said contact element to said ground circuit, with said resistor element being located within one foot of said contact element and further including second resistor element in said conductor and located spaced from said resistor element and adjacent to said ground circuit.

15. The system defined in claim 1 further including an electrical plug and a second resistor element, with said second resistor element being located at least partially in said electrical plug.

16. The system defined in claim 15 wherein said electrical plug includes a ground prong.

17. The system defined in claim 15 further including a test circuit.

18. The system defined in claim 15 and wherein said resistor element is physically located closely adjacent to said contact element.

19. The system defined in claim 15 wherein said electrical plug includes a prong positioned as a hot prong, said prong being non-conductive from said plug.

20. The system defined in claim 19 wherein said electrical plug further includes a neutral prong, said neutral prong being non-conductive from said plug.

21. The system defined in claim 15 wherein said electrical plug includes female receptacles.

22. The system defined in claim 15 wherein said electrical plug includes an internal resistor having a value of at least one megohm.

23. The system defined in claim 15 wherein said plug includes a plurality of grounding connectors.

24. The system defined in claim 15 wherein said plug includes a plurality of internal resistor elements.

25. The system defined in claim 1 further including a plug adapter and a second resistor element, with said second resistor element being at least partially located in said plug adapter.

26. The system defined in claim 25 further including an output lead from said plug adapter.

27. The system defined in claim 1 further including
   a Litz wire electrically connecting said electrostatic discharge contact element to said ground circuit.

28. The system defined in claim 27 further including a second resistor in series between said Litz wire and said ground circuit.

29. The system defined in claim 1 further including a second resistor element, with said resistor element being located closer to said contact element than said second resistor element and said second resistor element being located closer to said ground circuit than said resistor element.

30. The system defined in claim 1 wherein said inductor element is physically spaced apart from the resistor element in said discharge circuit.

31. The system defined in claim 1 further including additional equipment and wherein said discharge path is adapted to be electrically connected to said additional equipment.

32. The system defined in claim 1 further including a second electrostatic discharge contact element connected to said first resistor element.

33. The system defined in claim 32 wherein the electrostatic discharge contact element and the second electrostatic discharge contact element each includes a resistor element.

34. The system defined in claim 1 wherein said inductor element has an inductance which is greater than the distributed inductance of said ground system at the connection location between said inductor element and said ground system.

35. The system defined in claim 34 further including a second resistor element in series with said inductor element.

36. The system defined in claim 1 further including an electrical plug and wherein said inductor element is at least partially located in said electrical plug.

37. A system for protecting a person or equipment from surprise, damaging or uncomfortable electrostatic discharge (ESD) comprising:
- a headphone device;
- an electrostatic discharge contact element which is located in said headphone device;
- a discharge circuit electrically connected to said contact element, said discharge circuit including a first resistor element in series with said contact element and an inductor element in series with the first resistor element; and
- a ground circuit electrically associated with said discharge circuit.

38. The system defined in claim 37 wherein said headphone device includes two electrical conductors.

39. The system defined in claim 38 further including a resistor element connected to each conductor.

40. The system defined in claim 37 further including a jack on said headphone device to which said control circuit is releasably connected.

41. The system defined in claim 37 wherein said headset includes an ear pad and said first resistor element is part of said ear pad.

42. The system defined in claim 37 wherein said headphone device includes a headset pad.

43. The system defined in claim 32 wherein said headset pad has a resistance of at least 0.025 megohms.

44. The system defined in claim 37 wherein said discharge circuit is connected to an ear pad on said headphone device.

45. A system for protecting a person or equipment from surprise, damaging or uncomfortable electrostatic discharge (ESD) comprising:
- a ground system having stray inductance and resistance;
- an electrostatic discharge contact element; and
- an inductor electrically interposed in series between said contact element and said ground system and which is connected to said ground system at a connection location, said inductor element having an inductance which is greater than the stray inductance of said ground system at a connection location between said inductor element and said ground system.

* * * * *